United States Patent
Schütze

(10) Patent No.: US 7,318,999 B2
(45) Date of Patent: Jan. 15, 2008

(54) SUPPORT DEVICE FOR SEPARATING INDIVIDUAL OBJECTS FROM A BIOLOGICAL PREPARATION BY MEANS OF LASER IRRADIATION

(75) Inventor: Karin Schütze, Tutzing (DE)

(73) Assignee: P.A.L.M. Microlaser Technologies AG, Bernried (DE)

( * ) Notice: Subject to any disclaimer, the term of this patent is extended or adjusted under 35 U.S.C. 154(b) by 704 days.

(21) Appl. No.: 10/344,507

(22) PCT Filed: Aug. 16, 2001

(86) PCT No.: PCT/EP01/09468

§ 371 (c)(1),
(2), (4) Date: Feb. 10, 2003

(87) PCT Pub. No.: WO02/14833

PCT Pub. Date: Feb. 21, 2002

(65) Prior Publication Data
US 2003/0180941 A1    Sep. 25, 2003

(30) Foreign Application Priority Data
Aug. 16, 2000   (DE) ................................ 100 39 979

(51) Int. Cl.
*C12Q 1/00* (2006.01)
(52) U.S. Cl. .......................... 435/4; 422/255
(58) Field of Classification Search ...................... None
See application file for complete search history.

(56) References Cited
U.S. PATENT DOCUMENTS
4,046,457 A * 9/1977 Land et al. .................. 359/586

(Continued)

FOREIGN PATENT DOCUMENTS
DE    198 18 425 A1    7/1999

(Continued)

OTHER PUBLICATIONS

Schütze, K., H. Posl and G. Lahr; "Laser Micromanipulation Systems as Universal Tools in Cellular and Molecular Biology and in Medicine"; Cell Mol Biol 44(5) 1998: pp. 735-746.

(Continued)

*Primary Examiner*—Yelena G. Gakh
(74) *Attorney, Agent, or Firm*—Thelen Reid Brown Raysman & Steiner

(57) ABSTRACT

In order to separate individual, in particular biological, objects from a, in particular biological, preparation the use of a support device is proposed in which a laser light absorbent membrane (1), for example of polyester or polyethylene-naphthalene, to which the biological preparation for processing is to be applied is retained and tensioned, preferably together with carrier means (2) located thereunder, for example, a glass object carrier or a thicker membrane, by means of a retaining device (3, 4) configured in particular as a frame, so that a compact unit is provided. The support device according to the invention is particularly suitable for isolating individual biological objects from a surrounding biological material by means of laser irradiation and for catapulting said biological objects into a collecting device. The combination of a laser light absorbent membrane (1) and a laser light transparent membrane (2) as support for the laser light absorbent membrane (1) is particularly advantageous.

12 Claims, 2 Drawing Sheets

U.S. PATENT DOCUMENTS 5,294,695 A    3/1994  Lee et al.
5,750,347 A *  5/1998  Bagasra et al. ................ 435/6

FOREIGN PATENT DOCUMENTS

| DE | 298 23 783 U1 | 7/2000 |
| EP | 0 926 480 A2 | 6/1999 |
| EP | 0 993 964 A2 | 4/2000 |
| WO | WO 97/29355 | 8/1997 |
| WO | WO 98/35215 | 8/1998 |
| WO | WO 98/36261 | 8/1998 |

OTHER PUBLICATIONS

Emmert-Buck, Michael R., Michael R., et al.; "Laser Capture Microdissection"; XP 000644727; Published Aug. 11, 1996; pp. 998-1001.

Schütze, Karin and Annette Clement-Sengewald; "Catch and Move—Cut or Fuse"; Nature; Apr. 14, 1994; pp. 667-669; vol. 368.

* cited by examiner

SUPPORT DEVICE FOR SEPARATING INDIVIDUAL OBJECTS FROM A BIOLOGICAL PREPARATION BY MEANS OF LASER IRRADIATION

BACKGROUND OF THE INVENTION

1. Field of the Invention

The present invention relates to a support device for a preparation, in particular a biological preparation, which is suitable for isolating individual objects, in particular biological objects such as cells or chromosomes, contained in the preparation from the preparation by means of laser irradiation, and for thereby separating them from the preparation.

2. Description of Related Art

Generic support devices are used, for example in the field of microdissection, for sorting and harvesting individual biological cells. A corresponding process is described, for example, in WO 97/29355 A of the Applicant. This document describes how a selected biological object is separated from the surrounding biological mass located on a planar support, so that the selected biological object is prepared in isolation from the surrounding biological mass. For this purpose the selected biological object is cut out of the surrounding biological mass by means of laser irradiation. The biological object isolated in this way is then catapulted from the support to a collecting device by means of a laser shot, in which case the collecting device can be, for example, a collecting substrate or a collecting "cap". This method is generally used in combination with a suitable microscope arrangement to control the cutting and catapulting process in a microscope-supported manner. The laser beam for cutting out and/or catapulting a selected biological object can be controlled in a computerised manner. To harvest, i.e. separate, a single biological object it is not absolutely necessary to first carry out a cutting process and then a catapulting process by means of two separate laser irradiations; investigations have shown that, depending on the laser energy and the laser focus and on the constitution of the biological material to be treated, a single laser shot can be sufficient to separate the desired biological object directly from the surrounding biological mass and to catapult it into the collecting device.

The preparation to be processed with the laser irradiation is generally located on a glass object carrier. It can, however, also be located on a carrier membrane absorbent to the laser light used, which carrier membrane is cut together with the preparation in the course of the cutting process. In the subsequent catapulting process the isolated biological object together with the corresponding severed portion of membrane is catapulted into the collecting device. The use of such a carrier membrane is advantageous since relatively large objects can thereby be catapulted out completely using single laser shots, the carrier membrane acting as a tray with which relatively large areas can be transported and catapulted. Smaller biological objects such as filaments or chromosomes can be more easily isolated because they adhere to the carrier membrane and can then be catapulted morphologically intact into the collecting device together with the corresponding membrane portion in the catapulting process.

The handling of such a carrier membrane is, however, extremely problematic since this membrane is very thin, having a thickness in the range of micrometers. Together with the carrier membrane which serves to receive the preparation to be worked, a carrier transparent to laser light must therefore be used to carry or support the membrane. A glass object carrier of the kind used in known microscopes or the like is conventionally used for this purpose. The membrane is generally applied to the glass object carrier manually, i.e. the membrane is placed by the user on the glass object carrier and optionally fixed to the glass object carrier by the application of a special adhesive between the membrane and the glass object carrier.

This procedure is, however, relatively complex. Furthermore, because of the "waviness" of the membrane, individual gaps, which impede the laser treatment and the observation by microscope usually carried out concurrently, cannot be prevented from forming between the membrane and the object carrier. Such gaps also occur when applying an adhesive for bonding the membrane to the object carrier, since aqueous solutions or aqueous preparations (e.g. alcohol) are frequently used, in particular, in the field of biological, chemical or medical analyses or experiments, so that contact between the adhesive and water cannot be precluded, which has the undesired consequence when using a water-soluble adhesive that the membrane becomes detached from the object carrier.

SUMMARY

It is therefore the object of the present invention to provide a support device for a preparation, in particular a biological preparation, which is suitable for separating individual objects from the preparation by means of laser irradiation and which makes possible easier handling of the membrane used and therefore easier implementation of the separation process.

According to the invention a retaining device or retaining means is provided to tension the laser light absorbent membrane and thereby to solve the above-mentioned problem of waviness.

The membrane which is used to receive the preparation to be worked by means of laser irradiation can rest on a carrier means, the retaining means being configured to hold together the membrane and the carrier means. In this way a unit is formed between the membrane and the carrier means, i.e. the membrane and the carrier means are made available in the form of a "package", which simplifies handling of the support device as a whole.

The carrier means can be, for example, a conventional laser light transparent object carrier, in particular of glass, the retaining means taking the form, for example, of a, in particular, peripheral frame so that, on the one hand, the membrane is securely fixed to the object carrier and, on the other, is tensioned in order to prevent the formation of gaps between the membrane and the object carrier, or the formation of a "wavy" surface of the membrane. The membrane can be applied smoothly to the object carrier with the application of heat (e.g. by means of vacuum).

The carrier means can also be a relatively thick membrane as compared to the laser light absorbent membrane, for example of Teflon having a thickness of approx. 20 µm. In this case too the two membranes can be held together as a unit by retaining means taking the form of a frame.

It is especially advantageous to configure the retaining means according to the invention in the form of a Petri cup, the laser light absorbent membrane used to hold the preparation to be worked and a further membrane provided to support or carry said membrane being held in direct contact. In this way live cells or cell cultures can be cultivated in the Petri cup and are then catapulted from the laser light absorbent membrane by laser irradiation; the catapulting can take place directly or after prior cutting out.

A further embodiment according to the invention provides that the laser light absorbent membrane, which is cut out and catapulted together with the preparation located thereon by the laser irradiation, is fixed to the carrier means located below it, for example in the form of a glass object carrier or in the form of a thicker laser light transparent membrane (e.g. of Teflon), by means of an adhesive tape taking the form of a mask. In this case the adhesive tape is so applied that the laser-light absorbent membrane rests directly on the carrier means located below it and the marginal areas of this membrane are fixed by means of the adhesive tape to the carrier means located below it in order to tension the laser light absorbent membrane.

The laser light absorbent membrane according to the invention can consist, for example, of polyester or polyethylene-naphthalene. The polyethylene-naphthalene membrane has the advantage that it can be very easily cut by means of laser irradiation, for example UV laser irradiation, so that a very good cut line is produced with relatively low cutting energy. The use of a polyethylene-naphthalene membrane is appropriate and advantageous in particular in combination with glass object carriers. In order to cut objects, e.g. chromosomes or filaments located close together in a biological material, some degree of initial ablation of the biological material is required in order to make possible preparation of a pure sample. In this case the ablation is carried out with low laser energy. During ablation the membrane on which the biological material is located should not be damaged. In view of this the use of a polyester membrane can be advantageous, since this membrane makes possible selective ablation of the biological material located thereon without destruction of the membrane. The polyester membrane can therefore be used whenever very small biological objects, such as cell compartments, chromosomes, filaments or nucleus parts, are to be cut or catapulted from the surrounding biological material.

It should be noted in general that the combination of a laser light absorbent membrane with a carrier film located below it to support the first-mentioned membrane is advantageous because, in the case of a membrane-membrane combination, it is possible to work using a lens with short working distance, for example, a 100× lens, which is advantageous in particular when observing filaments or chromosomes. If normal glass object carriers (thickness 1 mm) are used satisfactory results can generally be achieved only with a lens having a longer working distance, for example a 40× lens.

Because cell fluids, etc., are frequently processed in the field of chemical, medical or biological analyses or experiments, at least the laser light absorbent membrane, which is used to receive the preparation to be processed and which is cut or catapulted together with the preparation, should be hydrophilised in order to prevent "beading" of the fluid located on this membrane and to make possible an even distribution of the fluid on the membrane. If a support or carrier film is used, this second membrane should advantageously also be hydrophilised. The hydrophilisation of the membranes can generally the carried out using conventional processes, for example plasma processes which result in ionisation of the membrane surface.

As described earlier, the present invention can preferably be used to process biological preparations and to separate individual biological objects, such as live or fixed biological cells or cell components, chromosomes or filaments, etc. The present invention is, however, also suitable for the laser treatment of non-biological objects and inanimate matter in order, for example, to isolate microscopically small objects of glass, silica or plastics material from a corresponding surrounding material. However, the present invention will be described below for clarification with reference to the example of the separation of individual biological objects from a biological mass or a biological preparation, preferred embodiments of the present invention being explained in particular.

DETAILED DESCRIPTION

Figure 1:
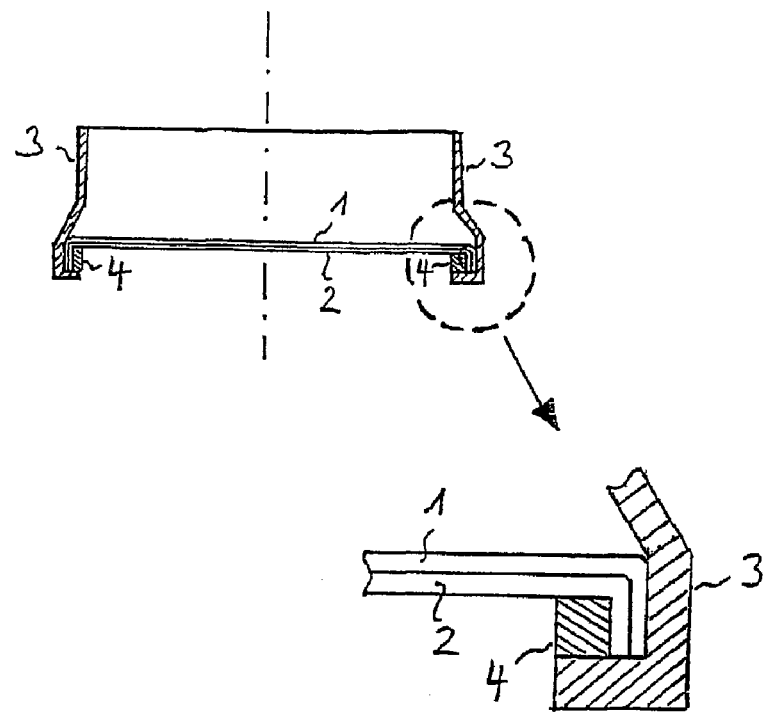
FIG. 1 is a representation of a support device according to a first embodiment of the present invention.

The support device shown in cross-section in FIG. 1 takes the form of a so-called Petri cup. In the present case this has a cylindrical main body 3 which is open at the top while the bottom is closed by a first membrane 2. This membrane 2 can consist, for example, of Teflon and can have a thickness of approx. 20 µm. The membrane 2 is clamped to the underside of the main body 3 by means of a peripheral circular ring 4, between said ring 4 and the main body 3, and is planar. Petri cups of this kind are generally known and are commercially obtainable. The particular advantage of such Petri cups and of the membrane 2 used therein lies in the fact that live cell cultures can be cultivated on the membrane 2.

According to the invention a further membrane 1, which is so constituted that it can be cut by means of laser irradiation and that objects can be (even directly) catapulted from it by means of the above-described laser catapulting effect, is arranged directly on the membrane 2. Accordingly, the membrane 1 must be laser light absorbent whereas the membrane 2 must not be damaged by the laser light during laser irradiation and should therefore be transparent to laser light. The laser light absorbent membrane 1, like the laser light transparent membrane 2, is tensioned between the ring 4 and the main body 3 of the Petri cup in such a way that a planar surface is produced. The two membranes 1 and 2 can optionally be bonded together or can adhere to one another.

The biological material to be worked is to be applied to the laser light absorbent membrane 1. The configuration of the support device according to the invention in the form of a Petri cup is advantageous in particular because cell cultures can be cultivated in the Petri cup which can then be immediately subjected to laser treatment to separate individual biological objects from the biological material without having to remove the cell cultures from the Petri cup and to apply them to a conventional object carrier.

For the laser treatment the Petri cup shown in FIG. 1 with the material located therein is positioned, for example, above a laser arrangement in such a way that the laser beam generated by the laser arrangement strikes the Petri cup from below and passes through the laser light transparent membrane 2, which serves as a base or support for the substantially thinner laser light absorbent membrane 1. Because the membrane 1 is a laser light absorbent membrane said membrane 1 with the biological material located thereon can now be cut by means of the laser beam by a suitable relative movement between the Petri cup and the laser beam, in order to cut out individual, previously selected biological objects from the surrounding biological material. Once the desired biological objects have been separated in this way the desired biological object with the corresponding severed portion of the laser light absorbent membrane 1 can be catapulted upwards into a suitable collecting device, for example a collecting substrate or collecting cap, by means of a single laser shot or separate laser shots. This is done on the basis of a laser-induced catapulting process which is explained in more detail in the above-mentioned WO 97/29355 A, to which reference is made in this context. A conventional (upright or inverted) microscope can, for example, be integrated into the laser arrangement in order to be able to select the desired biological objects in, for example, a computer-aided manner by microscope observation and then (also in a computerised manner) to separate them by laser irradiation. Investigations have shown that, depending on the constitution of the biological material to be worked, the type of laser, the laser energy set and the laser focus on the cutting process, [redundant 'and' omitted—Translator] individual biological objects can be catapulted from the biological material by means of one laser shot.

A pulsed laser emitting UV laser light is generally used for the laser treatment. This can be an $N_2$ laser, an excimer laser, an Nd:YAG laser or an Ar-ion laser, etc.

As already mentioned, the laser light absorbent membrane 1 on which the biological material to be worked is located is significantly thinner than the membrane 2 which serves as a support. A polyester membrane having a thickness of 0.9 μm-1 μm or a polyethylene-naphthalene membrane having a thickness of approx. 1.35 μm can, for example, be used as the laser light absorbent membrane 1. The polyethylene-naphthalene membrane is advantageous for the laser treatment of cell tissue, for example, because it can be very easily cut with relatively low laser energy. By contrast, the polyester membrane is advantageous if biological objects lying close together, such as chromosomes or filaments, are to be catapulted from the surrounding biological material, since in this case selective ablation of the surrounding biological material is frequently first necessary in order to obtain a sample, which in the case of a polyester membrane is possible without destruction of the membrane.

Altogether—as can be seen in FIG. 1—a very compact support device for a biological material to be treated by means of laser irradiation is provided, which support device can be manufactured in particular as a disposable article. Manual application of the laser light absorbent membrane 1 to the carrier material 2 located below it, which in the present case also takes the form of a membrane, is dispensed with. Because both membranes 1 and 2 are clamped between the main body 3 and the ring 4 a planar surface in particular of the membrane 1 and close contact between the membranes 1 and 2 are ensured. A "wavy" surface of both membranes is prevented in this way.

Figure 2:
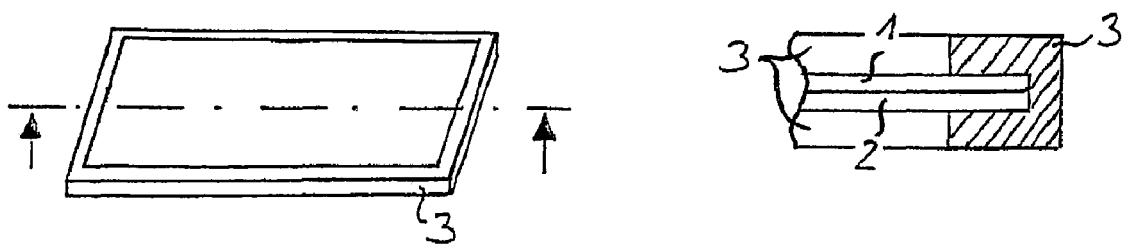
FIG. 2 is a representation of a support device according to a second embodiment of the present invention.

In FIG. 2 a second embodiment of a support device according to the invention is illustrated.

In FIG. 2, also, the laser light absorbent membrane is denoted by reference numeral 1 and the laser light absorbent membrane located below it and serving as a support or substrate for the laser light absorbent membrane is denoted by reference numeral 2. With regard to the constitution of the two membranes reference is made to the above discussion of the embodiment shown in FIG. 1. As can be seen in particular from the enlarged cross-sectional view of a marginal area of the support device shown in FIG. 2, the two membranes 1 and 2 are held together in such a way by a frame 3 which is made, for example, of plastics material that the two membranes 1 and 2 are located close together or in direct contact, so that altogether a compact unit is provided which is correspondingly easy to handle. In the embodiment shown in FIG. 2 the two membranes 1 and 2 are tensioned in the frame 3 which surrounds the entire periphery. Analogously to that in the embodiment shown in FIG. 1, therefore, the frame 3 performs in principle two functions, firstly, that of producing the planar surface of the two membranes 1 and 2 and, secondly, that of holding the two membranes 1 and 2 tightly together. The frame 3 can also be, for example, a flat metal frame, preferably of special steel.

As can be seen from FIG. 2, the support device illustrated takes the form of a conventional object carrier of the kind used in particular in commercially obtainable microscopes. For the laser treatment of the biological material located on the laser light absorbent membrane 1 the support device illustrated can be positioned, as explained with reference to the embodiment shown in FIG. 1, above (or—when using an upright microscope—below) a laser arrangement and irradiated, for example, with UV laser light in order to separate individual biological objects from the surrounding biological material and to catapult them into a collecting device.

In principle, instead of a laser light transparent membrane a rigid laser light transparent object can be used as the carrier or support for the laser light absorbent membrane 1 located upon it. In this case the support can be, in particular, a conventional glass object carrier which is commercially obtainable and has a thickness of, for example, approx. 1 mm or approx. 0.17 mm. In this case the laser light absorbent membrane, which is cut by the corresponding laser light and catapulted out together with the biological objects located thereon by means of a laser shot, is held firmly together with the glass object carrier 2 by means of the frame 3. Although the use of a glass object carrier is in principle suitable for the laser treatment of cell tissue, thin glass object carriers (thickness 0.17 mm) fracture very easily and normal glass object carriers (thickness 1 mm) are suitable only for lenses with a relatively long working distance. If a membrane-membrane combination is used, by contrast, lenses with a short working distance, e.g. 100× lenses, can also be used.

Figure 3:
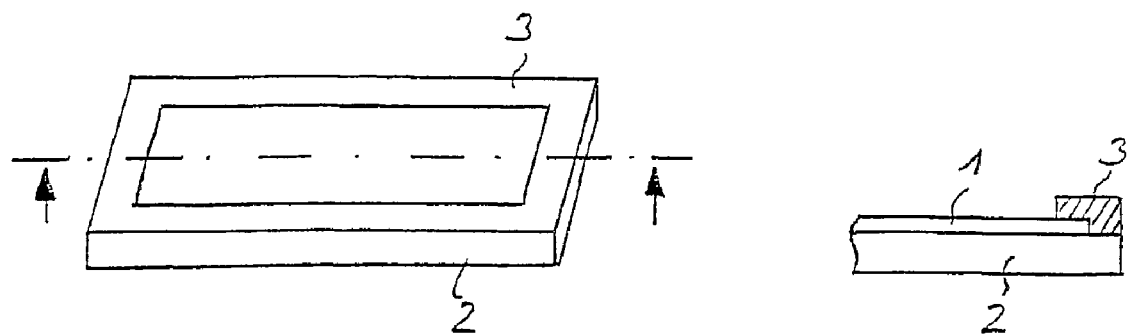
FIG. 3 is a representation of a support device according to a third embodiment of the present invention.

FIG. 3 shows a further embodiment of the present invention, on the one hand a perspective view and on the other hand an enlarged cross-sectional view of an edge portion of this embodiment being shown.

In the embodiment shown in FIG. 3 a conventional glass object carrier 2 on which a laser light absorbent membrane is supported is used as the carrier material. The laser light absorbent membrane 1 is held on the glass object carrier 2 by means of an adhesive agent or adhesive tape 3 running around, in particular, the entire periphery and having the form of a mask corresponding to the glass object carrier; i.e. the adhesive tape 3 takes the form of a rectangular edge, the inner edge portion lying on the lateral surface of the membrane 1 while the outer edge portion of the adhesive tape 3 lies on the outer surface of the glass object carrier, so that the laser light absorbent membrane and the glass object carrier 2 are held tightly together and an extremely compact unit which is correspondingly easy to handle is again provided.

Analogously to the embodiments shown in FIGS. 1 and 2 a support film can, of course, also be used instead of the glass object carrier. Regarding the constitution of the laser light absorbent membrane 1 and of the object carrier 2 or the corresponding carrier film, reference is again made to the embodiments previously described.

Figure 4:
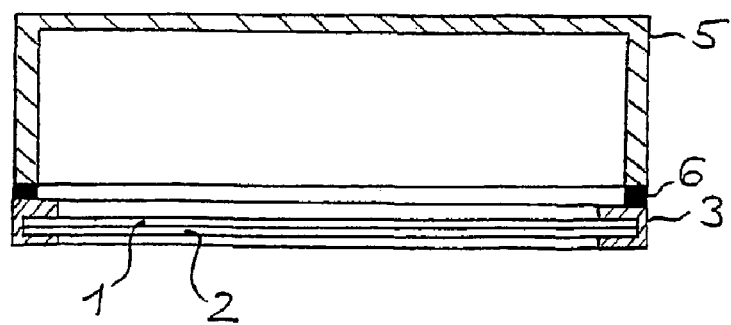
FIG. 4 is a representation of a support device according to a fourth embodiment of the present invention.

In FIG. 4 a further embodiment of a support device according to the invention is illustrated.

The support device shown in FIG. 4 has in principle a similar structure to the support device shown in FIG. 2 and is illustrated in a cross-sectional view. The support device therefore includes a frame 3 which holds together and tensions the laser light absorbent membrane 1 and the laser light transparent membrane 2 located below it and serving as a support or substrate for the laser light absorbent membrane. The frame 3 is made as thin as possible in order to enable the lens of the particular microscope used to be moved closer to the preparation located on the laser light absorbent membrane 1. In addition, with the shallowest possible frame 3 the collecting receptacle used to capture catapulted biological objects can be moved closer to the support device so that the biological objects can be catapulted out with a lower degree of scatter.

To supplement the embodiment illustrated in FIG. 2, according to FIG. 4 a parallelepiped-shaped receptacle 5 having an inlet connection for live (liquid) cell cultures is placed on the frame 3 and bonded thereto by means, for example, of a silicone adhesive 6. The interior of the receptacle 5 is therefore sealed in an airtight manner so that the cell cultures located in the receptacle 5 and on the laser light absorbent membrane 1 can grow in an incubator on the support device.

In order to use the support device illustrated in FIG. 4 in a laser-microdissection system of the above-described type the receptacle 5 can be ruptured from the frame 3 by exerting a suitable traction force, so that the support device remaining behind can be used in a similar way to that shown in FIG. 2. The fixing of the receptacle 5 to the frame 3 by means of the silicone adhesive 6 is therefore releasable.

Self-evidently, the receptacle can also be fixed to the support device or, preferably, to the frame 3 in a differently releasable manner, for example, by a vacuum fixing. Moreover, it is not absolutely necessary for the receptacle 5 to have a periphery adapted to the periphery of the surrounding frame 3, as in the embodiment shown in FIG. 4. The height of the receptacle 5 can be in the order of magnitude of, for example, 1 cm.

In the embodiments explained above and shown in FIGS. 1-4 a carrier means 2 was in each case used as the support for the laser light absorbent membrane 1. The use of a laser light absorbent membrane (see the embodiments represented in FIGS. 1, 2 and 4) as the carrier means 2 is advantageous, as compared to the use of a glass object carrier (see the embodiment represented in FIG. 3), in particular when using microscopes with high magnification, since a support membrane has better optical properties and therefore improves the microexamination capability.

The present invention is not, however, restricted to the use of a carrier means of the above-described type, but a carrier means 2 can also be dispensed with entirely, only the laser light absorbent membrane then being held and tensioned as above described in order to achieve a sufficient tautness of the laser light absorbent membrane 1. Such an arrangement is sufficient, in particular, if dry preparations are used. In this case the laser light absorbent membrane 1 can be bonded, for example, to the frame 3, which is sufficient in particular if the preparation placed on the laser light absorbent membrane 1 is subsequently subjected to no further chemical procedures. The manner illustrated in FIGS. 1-4 of retaining the laser light absorbent membrane 1 in the frame 3 without using an adhesive is, however, advantageous because of the improved resistance to chemicals if the preparation placed on the laser light absorbent membrane 1 is to be subjected to chemical procedures.

When using liquid preparations, for example live cells, the use of a carrier means 2 of the above-described type, in particular a support membrane, is advantageous, since otherwise, if only the laser light absorbent membrane 1 were used as the carrier for the biological material located thereon when cutting out and catapulting individual biological objects, fluid would flow through the resultant holes in the membrane 1.

The invention claimed is:

1. A support device for a biological preparation use in a laser microscope system for separating individual objects from the biological preparation by means of laser irradiation, comprising
   a UV laser light absorbent first membrane for receiving the biological preparation,
   a UV laser light transparent second membrane on which the UV laser light absorbent first membrane is directly arranged so that the UV laser light transparent second membrane carries the UV laser light absorbent first membrane, and
   retaining means which are so configured that they hold together the UV laser light absorbent first membrane and the UV laser light transparent second membrane and tension the UV laser light absorbent first membrane,
   wherein the UV laser light absorbent first membrane is thinner than the UV laser light transparent second membrane.

2. A support device according to claim 1, wherein the UV laser light absorbent first membrane is a polyethylenenaphthalene membrane.

3. A support device according to claim 2, wherein the polyethylenenaphthalene membrane has a thickness of approx. 1.35 µm.

4. A support device according to claim 1, wherein the UV laser light absorbent first membrane is a polyester membrane.

5. A support device according to claim 4, wherein the polyester membrane has a thickness of 0.9 µm-1 µm.

6. A support device according to claim 1, wherein the second membrane is made of UV laser light transparent Teflon.

7. A support device according to claim 1, wherein the second membrane has a thickness of approx. 20 µm.

8. A support device according to claim 1, wherein the UV laser light absorbent first membrane is hydrophilised.

9. A support device according to claim 1, wherein the retaining means are formed around the entire periphery of the UV laser light absorbent membrane and of the second membrane.

10. A support device according to claim 1, wherein the retaining means take the form of a frame which tensions the UV laser light absorbent first membrane and the second membrane.

11. A support device according to claim 10, wherein the UV laser light absorbent first membrane is fixed to the frame.

12. A support device according to claim 11, wherein the UV laser light absorbent membrane is adhered to the frame.

* * * * *